United States Patent
Shinar et al.

(10) Patent No.: US 6,432,362 B1
(45) Date of Patent: Aug. 13, 2002

(54) CHEMICAL SENSOR AND COATING FOR SAME

(75) Inventors: Ruth Shinar; Guojun Liu; Marc D. Porter, all of Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 09/413,401

(22) Filed: Oct. 6, 1999

(51) Int. Cl.[7] ............................................. G01N 27/00
(52) U.S. Cl. ............................ 422/82.01; 422/82.02; 73/24.06; 73/23.2; 73/31.05
(58) Field of Search .......................... 436/139, 527, 436/501; 205/775; 333/196; 204/403; 73/24.06; 422/82.02

(56) References Cited

U.S. PATENT DOCUMENTS

| | | | |
|---|---|---|---|
| 4,243,960 A | * 1/1981 | White et al. | 333/196 |
| 5,364,797 A | * 11/1994 | Olson et al. | 436/501 |
| 5,466,348 A | * 11/1995 | Holm-Kennedy | 205/775 |
| 5,478,756 A | * 12/1995 | Gizeli et al. | 436/527 |
| 5,512,882 A | 4/1996 | Stetter et al. | |
| 5,607,573 A | 3/1997 | Miller et al. | |
| 5,910,286 A | * 6/1999 | Lipskier | 422/68.1 |
| 5,936,150 A | * 8/1999 | Kobrin et al. | 73/24.06 |
| 6,106,149 A | * 8/2000 | Smith | 374/31 |
| 6,190,035 B1 | * 2/2001 | Smith | 374/31 |

OTHER PUBLICATIONS

U.S. patent application Ser. No. 60/065,349, Dilger et al., filed Nov. 12, 1997.

William H. King, Jr., Piezoelectric Sorption Detector, Analytical Chemistry, vol. 36, No. 9, Aug. 1964, pp. 1735–1739.

Jay W. Grate, Stephen J. Martin, and Richard M. White, Acoustic Wave Microsensors Part II, Analytical Chemistry, vol. 65, No. 22, Nov. 15, 1993, pp. 987–996.

Stephen J. Martin and Stephen D. Senturla, Dynamics and Response of Polymer–Coated Surface Acoustic Wave Devices: Effect of Viscoelastic Properties and Film Resonance, Analytical Chemistry, vol. 66, No. 14, Jul. 15 1994, pp. 2201–2219.

Jay W. Gate and Samuel J. Patrash, Method for Estimating Polymer–Coated Acoustic Wave Vapor Sensor Responses, Jul. 1,1995, Analytical Chemistry, vol. 67, No. 13, Jul. 1, 1995, pp. 2162–2169.

(List continued on next page.)

*Primary Examiner*—Jill Warden
*Assistant Examiner*—Brian Sines
(74) *Attorney, Agent, or Firm*—Marshall, Gerstein & Borun.

(57) ABSTRACT

An acoustic wave based-chemical sensor utilizing a crystal substrate and a coating of at least two blended materials is disclosed. The blended materials comprise a combination of (a) a high glass transition temperature polymer or a material of high melting point, and (b) a low glass transition temperature polymer or a material having a low melting point. Transducers are connected to the crystal substrate to generate an alternating potential across the crystal substrate, which in turn causes the crystal to resonate due to the converse piezoelectric effect. The blended coating absorbs the analyte, thus changing the mass of the chemical sensor, and accordingly changing its resonant frequency. The transducers detect this change in resonant frequency to indicate that the analyte is present. The use of blended materials results in a thicker coating combining the preferred properties of the blend constituents, such as improved detection sensitivities, faster response times, less acoustic wave damping, and higher operational temperature ranges.

17 Claims, 3 Drawing Sheets

OTHER PUBLICATIONS

Edward T. Zellers and Mingwei Han, Effects of Temperature and Humidity on the Performance of Polymer–Coated Surface Acoustic Wave Vapor Sensor Arrays, Analytical Chemistry, vol. 68, No. 14, Jul. 15, 1996, pp. 2409–2418.

Daniel A. Buttry and Michael D. Ward, Measurement of Interfacial Processes at Electrode Surfaces with the Electrochemical Quartz Crystal Microbalance, Chemical Reviews, 1992, vol. 92, No. 6, pp. 1355–1379.

K. K. Kanazawa, A General Solution for the Change in Mechanical Resonance of a Quartz Oscillator Due to Viscoelastic Overlayers, Apr. 30, 1986, pp. 1–22.

Ralph Lucklum, Carsten Behling, Richard W. Cernosek, and Stephen J. Martin, Determination of Complex Shear Modulus with Thickness Shear Mode Resonators, J. Phys. D: Appl. Phys. 30 1997, pp. 346–356.

Auge, et al., "Versatile Microcontrolled Gas Sensor Array System Using the Quartz Microbalance Principle and Pattern Recognition Methods," Sensors and Actuators B Chemical, vol. B26, part 1, pp. 181–186, May 1995.

Matsuno, et al., "A Quartz Crystal Microbalance–Type Odor Sensor Using PVC–Blended Lipid Membrane," IEEE Transactions on Instrumentation and Measurement, vol. 44, No. 3, pp. 739–742, Jun. 1995.

Lonergan, et al., "Array–Based Vapor Sensing Using Chemically Sensitive, Polymer Composite Resistors," IEEE Aerospace Applications Conference, No. 3, pp. 583–631, Feb. 1997.

Shiratori, et al., "Molecular Sifter Using Space Controlled Langmuir—Blodgett Films by Fullerene Molecules," Thin Solid Films, vol. 327–329, pp. 655–658, 1998.

\* cited by examiner

CHEMICAL SENSOR AND COATING FOR SAME

FIELD OF THE INVENTION

The present invention generally relates to systems for monitoring environmental contaminants and, more particularly, to systems for monitoring fugitive emissions from process equipment.

BACKGROUND OF THE INVENTION

Industrial plants which handle volatile organic compounds (VOCs) typically experience unwanted emissions of such compounds into the atmosphere from point sources, such as smoke stacks, and non-point sources, such as valves, pumps, and fittings installed in pipes and vessels containing the VOCs. Such VOCs include, but are not limited to, aromatics (e.g., benzene, toluene, ethylbenzene, and xylenes), halogenated hydrocarbons (e.g., carbon tetrachloride, 1,1,1-trichloroethane, and trichloroethylene), ketones (e.g., acetone, and methyl ethyl ketone), alcohols (e.g., methanol, ethanol, and propanol), ethers (e.g., dimethyl ether and methyl t-butyl ether), and aliphatic hydrocarbons (e.g., natural gas and gasoline).

Emissions from non-point sources, referred to as fugitive emissions, typically occur due to the leakage of the VOCs from joints and seals. Fugitive emissions from control valves may occur as the result of leakage through the packing between the valve stem and the body or bonnet of the valve. Valves employed in demanding service conditions involving frequent movement of the valve stem and large temperature fluctuations typically suffer accelerated deterioration of the valve stem packing, which results in greater fugitive emissions than valves employed in less demanding service.

While improvements in valve stem packing materials and designs have reduced fugitive emissions and lengthened the life of valve packing, the monitoring of fugitive emissions has become important as a means to identify and reduce fugitive emissions, and to comply with the more stringent regulation of emissions. For example, the Environmental Protection Agency (EPA) has promulgated regulations for specifying the maximum permitted emission of certain hazardous air pollutants from control valves, and requires periodic surveys of emissions from control valves.

Current methods of monitoring fugitive emissions involve manual procedures using a portable organic vapor analyzer. This manual method is time consuming and expensive to perform, and can also yield inaccurate results due to ineffective collection of the fugitive emissions from the equipment being monitored. If measurements are made on a valve exposed to wind, emissions from the valve may be dissipated before the analyzer can properly measure the concentration of the emissions. Also, if the analyzer is not carefully moved around the valve to capture all the emissions from the valve, an inaccurate measurement will result. Manual measurement methods also require plant personnel to dedicate a significant amount of time to making the measurements, thereby distracting plant personnel from other duties.

Automated monitoring and detection of fugitive emissions can yield significant advantages over existing manual methods. The EPA regulations require surveys of fugitive emissions at periodic intervals. The length of the survey interval may be monthly, quarterly, semi-annually, or annually, with the required surveys becoming less frequent if the facility operator can document a sufficiently low percentage of control valves exhibiting excessive leakage. Thus, achieving a low percentage of leaking valves reduces the number of surveys required per year. In a large industrial facility, where the total number of survey points can range from 50,000 to 200,000, a reduced number of surveys can result in large cost savings. By installing automated fugitive emission-sensing systems on valves subject to the most demanding service conditions, and thus, most likely to develop leaks, compliance with the EPA regulations can be more readily achieved for the entire facility.

However, employing chemical sensors in an industrial environment requires designing sensors that perform satisfactorily in the presence of high relative humidity across a broad temperature range. The sensors must be able to discriminate between the emissions of interest and other environmental contaminants, while retaining sufficient sensitivity to detect low concentrations of the fugitive emissions. A provision also must be made to enable periodic calibration of the sensors. The output signals from the fugitive emission sensing system must be suitable for input into plant monitoring and control systems typically found in process plants. This permits simple and inexpensive integration of the sensing system into existing plant process control systems.

The fugitive emission sensing system must be inexpensive to manufacture, and use a power source that is readily available in a typical process plant in order to keep installation costs to a minimum. The system must be suitable for use in hazardous areas subject to risk of explosion, requiring electrical equipment to be intrinsically safe or of an explosion-proof design. It also must be able to operate in harsh environments, including areas subject to spray washing, high humidity, high and low temperatures, and vibration. The system also must be simple and reliable, in order to keep maintenance costs to a minimum.

In certain applications, the sensors used to detect fugitive emissions are provided in the form of piezoelectric-based sensors having high sensitivities to surface mass changes, such that when an alternating potential is applied across the sensors, changes in resulting wave characteristics in the sensors, specifically the resonant frequency, indicate the presence of the analyte. More specifically, the sensors typically include a quartz crystal substrate with an outer layer made of material selected to most effectively absorb the analyte. Such outer coatings are selected to increase sensitivity, while reducing acoustic wave damping effects. In addition, such materials should be environmentally robust to accommodate the aforementioned wide temperature ranges, humidity ranges, and high levels of dust particles and other contaminants.

SUMMARY OF THE INVENTION

In accordance with one aspect of the present invention, a chemical sensor is provided which includes a substrate, at least two electrodes connected to the substrate, and a blended coating positioned over the substrate and the at least two electrodes. The blended coating includes at least two different materials.

In accordance with another aspect of the present invention, the blended coating includes (a) at least one high glass transition temperature polymer or at least one material of high modulus, like high melting point, and (b) at least one low glass transition temperature polymer, or at least one material of low modulus, like low melting point.

In accordance with another aspect of the present invention, the high glass transition temperature polymer can be, for example, polystyrene, poly(2,6-dimethyl-p- phenylene oxide), poly(methyl methacrylate), styrene/ maleic anhydride copolymer, poly(styrene-acrylonitrile), polyimide, polyaniline, poly(bisphenol A carbonate), poly (divinyl benzene), poly(methylstyrene), poly(phenylene sulfide), poly(vinylpyridine), poly(vinyl sulfone), and mixtures thereof, the low glass transition temperature polymer can be, for example, poly(diphenoxy phosphazene), poly (isobutylene), poly(chloroprene), polybutadiene, poly (ethylene oxide), poly(epichlorohydrin), and poly(dimethyl siloxane), and mixtures thereof, the material of low melting point can be, for example, APIEZON-H grease, chloroparafin, and mixtures 10 thereof, and the material of high melting point can be, for example, graphite, silica gel, and mixtures thereof In accordance with another aspect of the invention, the ratio of the low glass transition temperature polymer (or material of low modulus) to the high glass transition temperature polymer (or material of high modulus) is about 1:6 to about 40:1, and preferably is about 1:1 to about 4:1.

In accordance with yet another aspect of the present invention, a coating is provided for an acoustic wave based-chemical sensor wherein the coating includes a blend of at least two different materials.

These and other aspects and features of the present invention will become more apparent from the following detailed description when taken in conjunction with the accompanying drawings.

While the invention is susceptible of various modifications and alternative constructions, certain illustrative embodiments thereof have been shown in the drawings and will be described below in detail. It should be understood, however, that there is no intention to limit the invention to the specific forms disclosed, but on the contrary, the intention is to cover all modifications, alternative constructions, and equivalents, falling within the spirit and scope of the invention as defined by the appended claims.

DETAILED DESCRIPTION OF THE INVENTION

Figure 1:
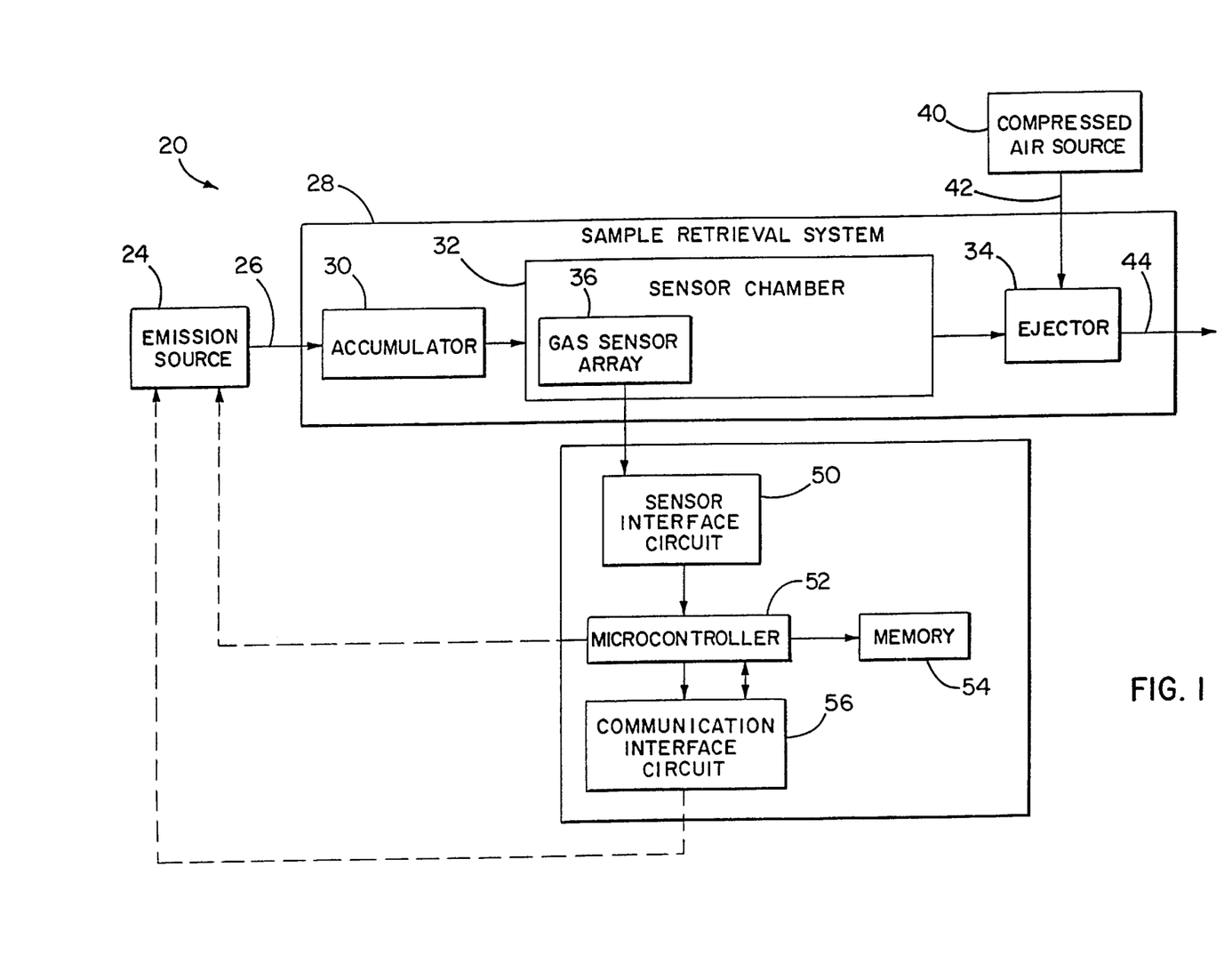
FIG. 1 is a block diagram of a fugitive emissions sensing system employing the present invention.

Referring now to the drawings, and with specific reference to FIG. 1, a fugitive emissions sensing system utilizing the present invention is generally depicted by reference numeral 20. However, it is to be understood that the present invention is primarily directed to a chemical sensor 22 (FIG. 2) which can be employed in a variety of applications, including applications separate from the fugitive emissions sensing system 20.

By way of overview, FIG. 1 is a block diagram of an illustrative fugitive emissions sensing system 20 employing the chemical sensor 22. An emission source 24 is shown, from which a sample stream 26 is drawn into sample retrieval system 28. The sample retrieval system 28 includes an accumulator 30, a sensor chamber 32, and an ejector 34.

Figure 2:
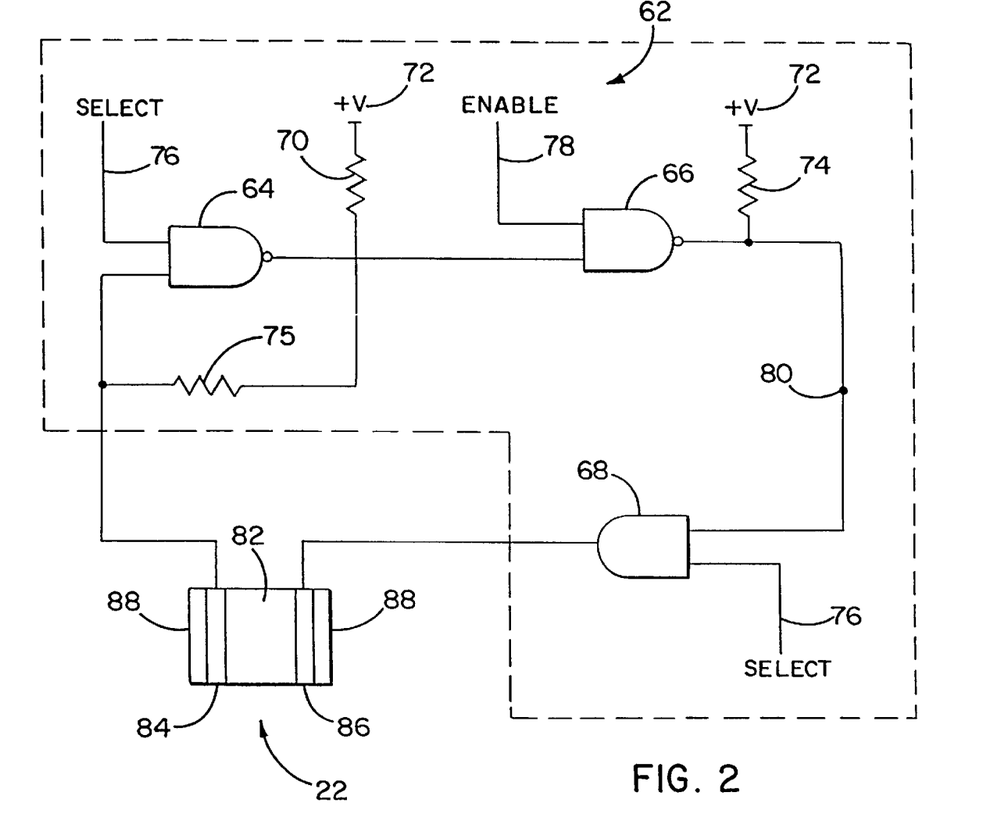
FIG. 2 is a schematic diagram of a chemical sensor circuit including a chemical sensor embodying the present invention.

A chemical sensor array 36 is located within the sensor chamber 32. The sample stream 26 is drawn from the accumulator 30 into the sensor chamber 32, exposing the chemical sensor array 36 to the sample stream 26. The chemical sensor array 36 contains one or more chemical sensors 22 (FIG. 2). The sample stream 26 then passes into the ejector 34. A compressed air source 40 provides compressed air 42 to the ejector 34, creating a pressure drop within the ejector 34 which draws a sample stream 26 through the sensor chamber 32 and into the ejector 34. The compressed air 42 and sample stream 26 are mixed within the ejector 34 and exhausted to atmosphere as a mixture 44.

The chemical sensor array 36 is connected to a sensor interface circuit 50, which processes the signals from the sensor array 36 and provides the process signals to a microcontroller 52. The microcontroller 52 stores the data from the sensors 22 in a memory 54, and uses the sensor data received from the fugitive emissions sensing system 20 to initiate control actions to reduce or eliminate the emissions. For example, the microcontroller 52 could close a valve upstream from the emissions source 24 to stop the flow of fluid through the emissions source 24 in order to stop emissions caused by the leakage of the fluid. Alternatively, the microcontroller 52 could alter operating conditions of the emissions source 24 itself to reduce or eliminate the fugitive emissions. The microcontroller 52 may use a communication interface circuit 56 to provide control signals to the upstream valve, the emission source 24, or any other equivalent that may be used to reduce or eliminate the emissions.

It can therefore be seen that the fugitive emissions sensing system 20 may be used to detect the presence of, or measure the concentration of, various types of fluids emitted from the emissions source 24. The system may be used to detect hazardous, toxic or polluting substances emitted from the source, or to detect leakage of non-hazardous substances, the loss of which may be a cause of concern. The fugitive emission sensing system 20 may be used to detect emissions from any kind of source, particularly industrial process equipment from which hazardous substances may leak. Examples include control valves, block valves, pumps installed on lines carrying hazardous gases, agitators, screw conveyors, or other equipment installed on process vessels containing hazardous fluids, heat exchanges, reactors, etc. When emissions are detected by the fugitive emissions sensing system 20, this data may be used by the fugitive emissions sensing system 20 to control the process in such a way as to reduce or eliminate the emissions.

As indicated above, the chemical sensor array 36 may include one or more chemical sensors 22 responsive to a particular analyte or fugitive emission being monitored. In the embodiment depicted in FIG. 2, the chemical sensor 22 is a quartz crystal microbalance (QCM) chemical sensor, but can be another type of piezoelectric acoustic wave devices, including surface acoustic wave (SAW) devices, acoustic plate mode (APM) devices, and flexural plate wave (FPW) devices. Fiber optic sensors and electrochemical sensors may also be used.

As shown in FIG. 2, the chemical sensor 22 may be connected to an oscillator circuit 62 for monitoring gas emissions. Alternatively, a network analyzer may be used. More specifically, the oscillator circuit 62 may include NAND gates 64 and 66, and an AND gate 68, connected in series. A resistor 70 may be connected between the output of the NAND gate 66 and the circuit power supply voltage 72, and a resistor 74 may be connected between the output of NAND gate 66 and circuit power supply voltage 72. A resistor 75 may be connected across the NAND gate 64, connecting a first input to the output. A select signal 76 may be connected to the second input of the NAND gate 64, and the same select signals may also be connected to an input of the AND gate 68. An enable signal 78 may be connected to an input of the NAND gate 66. When the select signal 76 and the enable signal 78 are both high, the NAND gates 64 and 66 act as high-gain inverting amplifiers and cause an oscillator 80 to oscillate between high and low voltage, producing an oscillating square wave output. The oscillating voltage from the oscillator output 80 may be transferred through the AND gate 68 and applied across the chemical sensor 22 causing the chemical sensor 22 to physically resonate.

In order to appreciate the significance of this resonance, it is first important to understand that the chemical sensor 22 utilizes the converse piezoelectric effect. By way of background, the piezoelectric effect holds that a mechanical stress applied to the surfaces of various crystals, including quartz, affords a corresponding electrical potential across the crystal having a magnitude proportional to the applied stress. The electrical charge generated in the quartz crystal under stress is due to the shift of dipoles resulting from the displacement of atoms in the crystalline material. The converse piezoelectric effect holds that application of a voltage across certain crystals, including quartz crystals, results in a corresponding mechanical strain in the crystal. In quartz, this strain or deformation is elastic. It follows that an alternating potential across the crystal causes a vibrational motion in the quartz crystal, i.e., the aforementioned resonance. The chemical sensor 22 therefore includes a crystal substrate 82 which interacts with the oscillating circuit 62, and in turn causes the oscillator circuit 62 to oscillate at the resonant frequency of the chemical sensor 22. Thus, the frequency of the oscillator output 80 will vary as the resonant frequency of the chemical sensor 22 varies.

The resonant frequency of the chemical sensor 22 can vary based on a number of parameters, including the mass, size, shape, and cut of the quartz crystal substrate 82. Quartz crystal exhibits a natural resonant frequency that is a function of the mass and structure of the crystal. The precise size, type of cut, and thickness of the quartz crystal substrate 82 are selected to result in a particular resonant frequency. For example, an AT-cut crystal with a nominal resonant frequency of 8–30 megahertz is suitable for chemical sensor applications. Suitable quartz crystal substrates may be obtained from Standard Crystal Corporation of California. Other types of suitable materials to serve as the substrate include lithium niobate ($LiNbO_3$), which is particularly suited for a surface acoustic wave (SAW) based-sensor; and aluminum nitride (AlN), which is particularly suited for a thin film resonator based-sensor.

In order to apply the alternating potential across the substrate 82, first and second electrodes 84 and 86 are connected to the crystal substrate 82 and may be constructed of gold, although other suitable corrosion-resistant and acoustically compatible conductors may be used, possibly including aluminum, palladium, chromium, chromium-on-gold, and graphite. The electrodes 84 and 86 may serve as both the conductors for generating the alternating current across the crystal substrate 82, and as transducers for sensing parameters related to changes in resonant frequencies resulting in the crystal substrate 82.

As indicated above, the resonant frequency of the chemical sensor 22 is a function of the total mass of the device. Therefore, the mass of any coating provided around the crystal substrate 82 also affects the total mass of the device, and thereby affects the resonant frequency of the chemical sensor 22. The coatings provided about the crystal substrate 82 are selected to absorb molecules of the analyte. When analyte molecules are absorbed by the coating, the mass of the coating is slightly increased, which in turn increases the mass of the entire chemical sensor 22, and thus changes the resonant frequency of the chemical sensor 22. The resonant frequency of the chemical sensor 22 is also a function of the viscoelastic properties of the coatings and mechanical stresses caused by temperature effects in the chemical sensor mounting structure. However, these effects are either negligible or can be compensated for. Thus, a very sensitive chemical detector may be constructed by selecting a coating that has a chemical affinity with the particular analyte of interest. The quantity of molecules absorbed and deposited, and the resulting change in the operating frequency of the oscillator circuit 62, is a function of the concentration of the analyte being measured in the environment surrounding the chemical sensor 22. The frequency changes linearly with changes in analyte concentration, within certain limits.

Thus, a change in the concentration of the analyte of interest can be measured by measuring the change in the frequency of the oscillator output 80. The chemical sensor 22 can be calibrated by exposing the chemical sensor 22 to known concentrations of the analyte and recording the resulting frequency of the oscillator output 80. The chemical sensor 22 then can be used to measure the absolute concentration of the analyte by comparing the measured frequency to the aforementioned recorded values.

The particular coating chosen for the crystal substrate 82 should preferably readily absorb the molecules of the analyte, to provide a high degree of sensitivity to the analyte, but do so without damping the generated waves. The coating also should be suitable for use in a wide temperature range with fast response and recovery times. The present invention provides such a coating in the form of a blended coating 88.

Low glass transition temperature polymers, and some materials having a low melting point or low modulus, are attractive as coating materials for such sensors due to their selective, rapid, and reversible responses to volatile organic compounds. However, low glass transition temperature polymers have low shear modulus, and therefore exhibit a relatively large damping effect on acoustic waves. The damping or attenuation of the acoustic waves increases as coating thickness increases, or as ambient temperature increases. This combination of features dictates that coatings of low glass transition temperature polymers be of a limited thickness and be exposed to a limited temperature range. However, since the chemical detection sensitivity of acoustic wave-based sensors is generally proportional to coating thickness, coatings of low glass transition temperature polymers, which are necessarily thin, are accordingly limited in their detection sensitivity. The performance of low melting point materials as coatings generally resembles that of low glass transition temperature polymers. Additionally, the operational temperature range of low melting point materials used as coatings is necessarily limited by their low melting point.

High glass transition temperature polymers exhibit characteristics generally opposite to those of low glass transition temperature polymers when used as chemical sensing coatings. More specifically, because high glass transition temperature polymers, and materials having a high melting point, have relatively large shear moduli, they exhibit less damping or attenuating effects on acoustic waves over a wide temperature range. Consequently, a thicker coating of a high glass transition temperature polymer can be used, which in turn increases sensitivity by allowing mass uptake of the analyte. However, high glass transition temperature polymers exhibit extremely slow and hysteresis responses unless used as very thin coatings.

The blended coating 88 of the present invention, which is a combination of (a) at least one high glass transition temperature polymer or high melting point material, and (b) at least one low glass transition temperature polymer or low melting point material, results in a coating having the preferred properties of the blend constituents. The blended coatings 88 therefore can have tailored sorption properties, increased detection sensitivities, improved response times, reduced acoustic losses, and enhanced sensor performance over a wide temperature range.

For the purpose of this application, high glass transition temperature polymers are defined as polymers having a glass transition temperature of about 25° C., or greater. For example, polystyrene has a $T_g$ of about 100° C., and poly(2,6-dimethyl-p-phenylene oxide) has a $T_g$ of about 210° C. Low glass transition temperature polymers are defined as polymers having a glass transition temperature of less than about 25° C. For example, poly(diphenoxy phosphazene) has a $T_g$ of −8° C., poly(choloroprene) has a $T_g$ of −45° C., and poly(isobutylene) has a $T_g$ of −73° C. Low melting point materials are defined as materials having a melting point of less than 50° C., but no lower than 25° C. High melting point materials are defined as materials having a melting point of 50° C., or greater, and preferably in the range of about or above 100° C.

To illustrate the invention, examples of different blends are described below in detail. The high glass transition temperature polymers used in these examples were polystyrene (PS) and poly(2,6-dimethyl-p-phenylene oxide) (PPO). The low glass transition temperature polymers used were poly(diphenoxy phosphazene) (PDPP) and poly (isobutylene) (PIB). The low melting point materials used was APIEZON-H® grease, manufactured by M & I Materials, Ltd. Other examples of suitable high glass transition temperature polymers include, but are not limited to, poly(methyl methacrylate), styrene/maleic anhydride copolymer, poly(styrene-acrylonitrile), polyimide, polyaniline, poly(bisphenol A carbonate), poly (divinylbenzene), poly(methylstyrene), poly(phenylene sulfide), poly(vinylpryidine), and poly(vinyl sulfone). Examples of other suitable low glass transition temperature polymers include, but are not limited to, poly(chloroprene), polybutadiene, poly(ethylene oxide), poly(epichlorohydrin), poly(dimethyl siloxane), and other polysiloxanes. Examples of other suitable high melting point materials include, but are not limited to, graphite and silica gel. An example of another suitable low melting point material is chloroparafin. However, it is to be understood that such examples are only exemplary of the invention, and that the invention includes blends of other polymers and materials, in addition to those specifically listed or described.

Poly(diphenoxy phosphazene) and Polystyrene Blend

The blending of high and low glass transition temperature polymers results in a coating having regions of high glass transition temperature polymer interspersed among regions of low glass transition temperature polymer. Such a structure provides a coating having physical crosslinking to a degree that restricts the damping effects observed in low glass transition temperature polymers, while preserving the reversible and fast response time of low $T_g$ polymers and the sensitivity of high $T_g$ polymers.

The coating 88 according to this embodiment may be manufactured by dissolving 1% to 3%, by weight, poly (diphenoxy phosphazene) (PDPP), a low glass transition temperature polymer, and 1% to 3%, by weight, polystyrene (PS), a hihg glass transition temperature polymer, in a solvent, preferably tetrahydrofuran or toluene. The PDPP and PS can be blended at a range of ratios, i.e., about 1:6 to about 40:1, preferably about 1:3 to about 10:1. A PDPP:PS ratio of about 1:1 to about 3:1 is most preferred. Such preferred ratios exhibit fast, linear, and reversible responses to VOCs, such as toluene, for example. Solutions containing a PDPP:PS ratio of 1:6, 1:3, 1:1, 3:1, 10:1, and 40:1 were prepared fortesting.

The blended coating 88 components can be dissolved in one common solvent, or in a mixture of solvents. A common solvent is preferred in order to achieve a coating of homogeneous distribution of discrete domains of the two (or more) blended constituents. Mixtures of solvents that evaporate at different rates, one of which dissolves preferably one constituent, can be used to achieve coatings of different properties, composed of continuous phases rather than discrete domains.

The resulting solution is applied to any of the aforementioned substrates and electrodes, with the preferred embodiment being a 8–30 MHZ quartz crystal substrate with chromium/gold electrodes attached thereto. The substrate 82 and electrodes 84, 86 then can be placed on a spin coater, i.e., a machine adapted to rotate at variable speed, e.g., 500–6000 RPM. In addition to such a spin coating technique, the coating also can be applied by any other conventional method, such as dipping or spraying. The coated substrate and electrodes then are cured at, for example, about 65° C. to about 75° C. for about 5 hours. Such a process results in a coating 88 preferably having a thickness of about 0.7 microns to about 5.7 microns.

The benefits of such a coating were tested with a network analyzer, which measured the reflection coefficients of the sensor 22 as a function of frequency, and equivalent circuit analysis, which monitored the resonant frequency and determined certain electrical circuit parameters including series resistance. More specifically, the network analyzer outputs a sine wave signal in a preprogrammed frequency range, typically from 8.5 to 12.5 MHZ, and enables the sensor 22 to oscillate at its fundamental resonant frequency. From the signal reflected from the sensor under test, its resonant characteristics including resonant frequency, series resistance, inductance, and capacitance are extracted using the equivalent circuit analysis. The attenuation of acoustic waves can be observed from an increase in the series resistance. The increase in resistance adds noise to the measurement, reducing the low detection limit, and can potentially lead to a complete cessation in oscillation.

When the sensors 22 manufactured according to this example were tested, their series resistance generally increased with increased coating thickness and ambient temperature. For example, PDPP coatings of 2.3 microns and 2.8 microns exhibited resistance values of 36 ohms, and 64 ohms, respectively, at 25° C. Upon heating to 50° C., the resistance values increased to 150 ohms, and 345 ohms, respectively. However, using a blended solution having a PDPP:PS ratio of 1:1, a coating having a thickness of up to 5.7 microns had significantly lower resistance values than a PDPP coating alone. For example, the resistance value for a 4.8 micron coating was 50 ohms, at 25° C. The resistance value increased to only 75 ohms upon heating to 50° C. The responses of such a blended coating to toluene at 25° C. were linear, rapid, and reversible.

Poly(isobutylene) and Poly(2,6 dimethyl-p-phenylene oxide) Blends

Poly(2,6-dimethyle-p-phenylene oxide) (PPO) normally cannot be used in chemical sensor applications because its response time to VOCs is extremely slow due to the stiffness of such a high glass transition temperature polymer. Unlike most polymers, however, the series resistance of transducers coated with PPO decrease when heated from 25° C. to 50° C. Conversely, coatings of poly(isobutylene) (PIB) show fast responses, but exhibit large damping at high temperatures or when thick coatings are used. However, a blend of the two results in a coating with response time better than PPO alone, and one which shortens as ambient temperature increases. Additionally, the attenuation of the acoustic waves at high temperatures is reduced in comparison to PIB alone. One useful application of such a PIB:PPO coating is therefore in elevated temperature operation environments. For example, a PIBPPO coating having a ratio of 4:1 and a thickness of about 2.2 microns was successfully used at temperatures of 25° C. and 50° C. It is envisioned that higher operational temperatures are possible. Coatings with a higher PIB:PPO ratio (relatively more PIB) can be used at lower temperatures.

Figure 3:
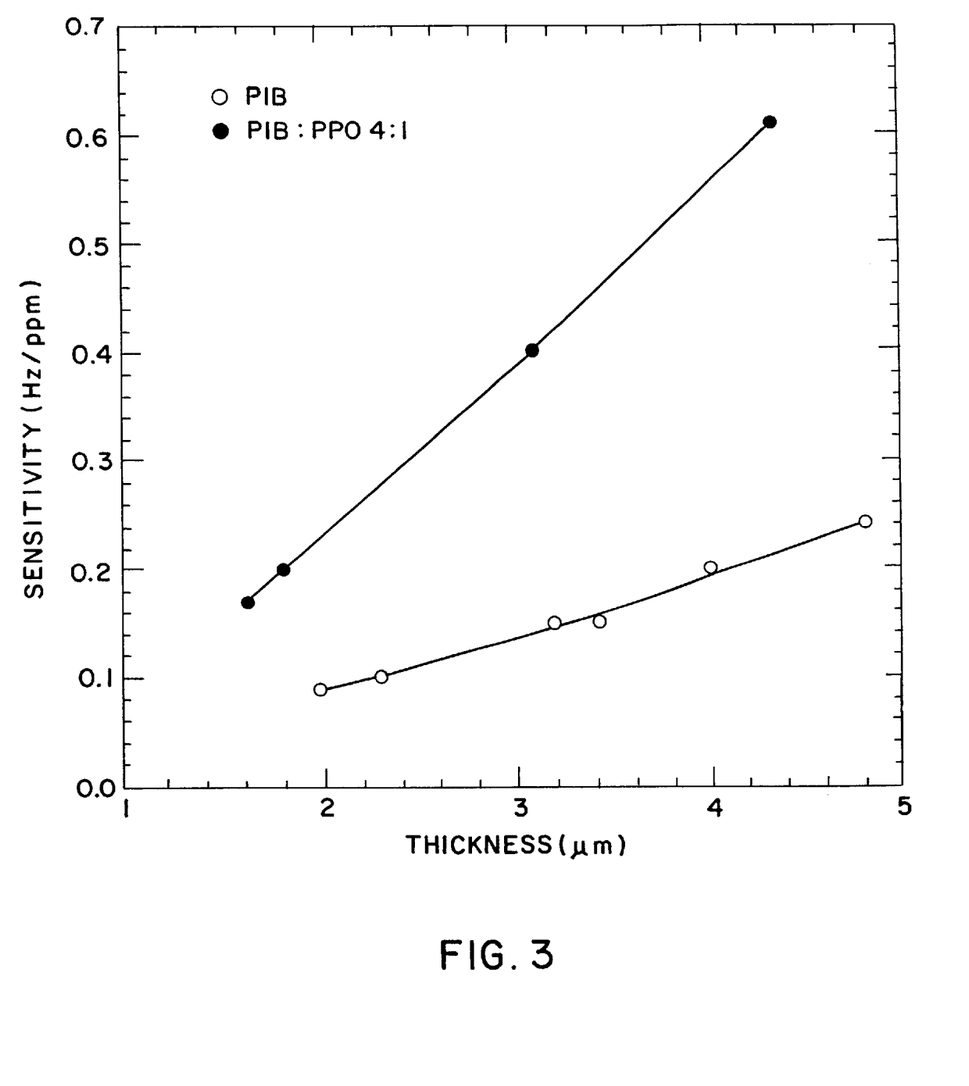
FIG. 3 is a graph plotting the sensitivity of a sensor built in accordance with the present invention vs. coating thickness.

The normalized sensitivity (sensitivity normalized to the coating thickness) of a 4:1 PIB:PPO coating toward toluene increased by a factor of 1.7 at 25° C., and 2.9 at 50° C. in comparison to PIB alone (see FIG. 3). To achieve sensitivity to toluene with the PIB alone that is comparable to that of a PIB:PPO coating having a thickness of 2.2 microns, the thickness of the PIB coating had to be increased to such a value that the thickness resulted in impermissibly high attenuation of the acoustic waves.

The coating according to this embodiment can be manufactured using the same dissolving, spin coating (or other conventional application techniques), and curing steps referenced above with regard to the PDPP and PS blend.

APIEZON-H Grease and Polystyrene Blends

This embodiment utilizes the fast and reversible response of APIEZON-H grease (AP-H), a low modulus, hydrocarbon material, and the superior acoustic wave properties of polystyrene (PS), a high glass transition polymer.

The coating 88 can be manufactured by dissolving AP-H and PS in toluene. The concentrations of AP-H and PS can be in the range of about 2 to about 20%, and about 1 to about 6%, by weight, respectively. The ratio of AP-H to PS can range from about 1:1 to about 10:1, preferably, about 2:1 to about 6:1, with a ratio of about 3:1 being most preferred because of a response time of less than four minutes and an operational temperature range of about –10° C. to about 50° C.

The resulting solution then is applied to the substrate 82 and electrodes 84, 86 using the aforementioned spin coating technique, or any other conventional technique, such as spraying or dipping. The coating 88 is then air dried and baked at, for example, about 65° C. to about 85° C.

In testing, the series resistance of the coated sensor 22 was used as a key criterion for the evaluation of the acoustic wave properties of the coating 88. The results showed that the series resistance increased with increasing coating thickness and temperature, but to a lesser degree than for devices using AP-H alone. Since the blended coating 88 exhibited improved acoustic properties, thicker and therefore more sensitive coatings could be used over the temperature range studied. The detection sensitivities of the coating 88 improved with the addition of PS, the level of which was optimized at the aforementioned 3:1 ratio in light of the associated increase in response time. A larger level of PS is recommended for applications in higher temperature environments where responses become faster, but sensitivity and temperature stability become more critical parameters. For lower temperature applications, where long response times hinder performance, but detection sensitivity is high, a lower content of PS is recommended.

The actual response time (i.e., the time required to attain ninety percent of the saturation value) of the sensors 22 is related to the ratio of the coating components. As the relative level of the high $T_g$ polymer or material or high modulus in the blended coating increases, the response time increases. The response time also is a function of the coating thickness and the measurement temperature, i.e., as the coating thickness increases the response time becomes longer, and as the temperature decreases, the response time becomes longer. For example, over the temperature range of –10° C. to 50° C., the response times typically ranged from 1 to 9 minutes.

Figure 4:
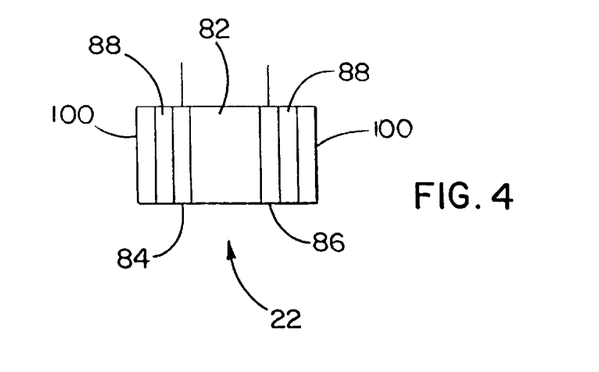
FIG. 4 is an alternative embodiment of a chemical sensor having first and second coatings thereon.

In an alternative embodiment shown in FIG. 4, a second coating 100 can be positioned over the coating 88. The second coating 100 is chosen to enhance responsiveness characteristics and detection sensitivity. For example, a second coating that is hydrophobic can reduce interference of water vapor. A second coating that is hydrophilic or contains tailored functional groups, such as amines, carboxylates, of OH groups, can enhance selectivity an specificity in analyte detection. The thickness of the second coating 100 may be provided at a range of thicknesses, with about 0.2 to about 1.5 being preferred.

From the foregoing, it can therefore be seen that the present invention provides an improved acoustic-wave based sensor having a blended coating of two or more materials. The blended coating combines the preferred sensing properties of each of the blended materials.

What is claimed is:

1. A chemical sensor, comprising:
   a substrate;
   at least two electrodes connected to the substrate; and
   a blended coating positioned over the substrate and at least one of the electrodes, the blended coating comprising at least two different materials, wherein the combination of the substrate and the blended coating has a first resonant frequency in the presence of a chemical having a first concentration and a second resonant frequency in the presence of the chemical having a second concentration.

2. A chemical sensor, comprising:
   a substrate;
   at least two electrodes connected to the substrate; and
   a blended coating positioned over the substrate and at least one of the electrodes, the blended coating comprising (a) a first glass transition temperature polymer, or material having a first modulus value, and (b) a second glass transition temperature polymer, or material having a second modulus value, wherein the first glass transition temperature is greater than the second glass transition temperature and the first modulus value is greater than the second modulus value, wherein the combination of the substrate and the blended coating has a first resonant frequency in the presence of a chemical having a first concentration and a second resonant frequency in the presence of the chemical having a second concentration.

3. The chemical sensor of claim 2 wherein the first glass transition temperature polymer has a glass transition temperature greater than 25° C.

4. The chemical sensor of claim 2 wherein the second glass transition temperature polymer has a glass transition temperature less than 25° C.

5. The chemical sensor of claim 2 wherein the first modulus material has a melting point of greater than 50° C.

6. The chemical sensor of claim 2 wherein the second modulus material has a melting point of less than 50° C.

7. The chemical sensor of claim 2 wherein the first glass transition temperature polymer is selected from the group consisting of polystyrene, poly(2,6-dimethyl-p-phenylene oxide), poly(methyl mathacrylate), styrene/maleic anhydride copolymer, poly(styrene-acrylonitrile), polyimide, polyaniline, poly(bisphenol A carbonate), poly(divinyl benzene), poly(methylstyrene), poly(phenylene sulfide), poly(vinylpyridine), poly(vinyl sulfone), and mixtures thereof.

8. The chemical sensor of claim 2 wherein the second glass transition temperature polymer is selected from the group consisting of poly(diphenoxy phosphazene), poly(isobutylene), poly(chloroprene), polybutadiene, poly(ethylene oxide), poly(epichlorohydrin), poly(dimethyl siloxane), and mixtures thereof.

9. The chemical sensor of claim 2 wherein the first modulus material is selected from the group consisting of graphite, silica gel, and mixtures thereof.

10. The chemical sensor of claim 2 wherein the second modulus material is selected from the group consisting of APIEZON-H® grease, chloroparafin, and mixtures thereof.

11. A chemical sensor, comprising:

a substrate;

at least two electrodes connected to the substrate; and a blended coating positioned over the substrate and at least one of the electrodes, the blended coating comprising (a) polystyrene and (b) a first material selected from the group consisting of APIEZON-H® grease, chloroparafin, and mixtures thereof.

12. The chemical sensor of claim 11 wherein a ratio of the first material to the polystyrene is about 1:1 to about 10:1.

13. The chemical sensor of claim 2 wherein the first glass transition temperature polymer comprises polystyrene and the second glass transition temperature polymer comprises poly(diphenoxy phosphazene).

14. The chemical sensor of claim 13 wherein a ratio of the poly(diphenoxy phosphazene) to the polystyrene is about 1:6 to about 40:1.

15. The chemical sensor of claim 13 wherein the blended coating has a thickness of about 0.7 microns to 5.7 microns.

16. The chemical sensor of claim 2 wherein the first glass transition temperature polymer comprises poly(2,6-dimethyl-p-phenylene oxide) and the second glass transition temperature polymer comprises poly(isobutylene).

17. The chemical sensor of claim 1, wherein the first concentration of the chemical is approximately a zero concentration.

\* \* \* \* \*

UNITED STATES PATENT AND TRADEMARK OFFICE
CERTIFICATE OF CORRECTION

PATENT NO.   : 6,432,362 B1
DATED        : August 13, 2002
INVENTOR(S)  : Shinar et al.

It is certified that error appears in the above-identified patent and that said Letters Patent is hereby corrected as shown below:

Column 8,
Line 13, please replace "fortesting[i]" with -- for testing --.

Column 10,
Line 27, please replace "of" with -- or --.
Line 27, please replace " an" with -- and --.

Signed and Sealed this

Eighth Day of April, 2003

JAMES E. ROGAN
*Director of the United States Patent and Trademark Office*